(12) United States Patent
Huang et al.

(10) Patent No.: US 11,111,317 B2
(45) Date of Patent: Sep. 7, 2021

(54) CORDYCEPS MILITARIS MEDIUM POLYSACCHARIDE, METHOD FOR SEPARATING AND PURIFYING SAME, AND USE THEREOF

(71) Applicant: SOUTH CHINA NORMAL UNIVERSITY, Guangzhou (CN)

(72) Inventors: Ruqiang Huang, Guangzhou (CN); Jingwen Zhang, Guangzhou (CN); Jinghui Wang, Guangzhou (CN); Qian Wang, Guangzhou (CN); Linlin Gao, Guangzhou (CN)

(73) Assignee: SOUTH CHINA NORMAL UNIVERSITY, Guangzhou (CN)

( * ) Notice: Subject to any disclaimer, the term of this patent is extended or adjusted under 35 U.S.C. 154(b) by 0 days.

(21) Appl. No.: 16/770,983

(22) PCT Filed: Dec. 12, 2018

(86) PCT No.: PCT/CN2018/120506
§ 371 (c)(1),
(2) Date: Jun. 9, 2020

(87) PCT Pub. No.: WO2019/205662
PCT Pub. Date: Oct. 31, 2019

(65) Prior Publication Data
US 2020/0369789 A1   Nov. 26, 2020

(30) Foreign Application Priority Data
Apr. 27, 2018 (CN) .......................... 201810389081.7

(51) Int. Cl.
*C08B 37/00* (2006.01)
*A61P 19/06* (2006.01)
*A61K 31/715* (2006.01)

(52) U.S. Cl.
CPC .......... *C08B 37/006* (2013.01); *A61K 31/715* (2013.01); *A61P 19/06* (2018.01); *C08B 37/0003* (2013.01)

(58) Field of Classification Search
None
See application file for complete search history.

(56) References Cited

FOREIGN PATENT DOCUMENTS

| CA | 102417544 A | 4/2012 |
|---|---|---|
| CN | 102731666 A | 10/2012 |
| CN | 104497160 A | 4/2015 |
| CN | 104725521 A | 6/2015 |
| CN | 105085704 A | 11/2015 |

OTHER PUBLICATIONS

Zhu, CN 102731666 A, Oct. 17, 2012, machine translation. (Year: 2012).*
Chen X.L. et al "Structural characterization of a polySaccharide from cultured cordyceps militaris with antioxidant activity" (Science and Technology of Food Industry Jun. 23, 2016.
Ren, Da-ming, Dong-qi Li, and Yun-yun Lao. "Purification and composition analysis of polysaccharides from Cordyceps militaris solid fermentation medium [J]." Science and Technology of Food Industry 10 (2010).
Ma, Li, et al. "Hypouricemic actions of exopolysaccharide produced by Cordyceps militaris in potassium oxonate-induced hyperuricemic mice." Current microbiology 69.6 (2014): 852-857.

* cited by examiner

*Primary Examiner* — Layla D Berry
(74) *Attorney, Agent, or Firm* — JMB Davis Ben-David (57) ABSTRACT

A *Cordyceps militaris* medium polysaccharide, a method for separating and purifying same, and the use thereof, wherein the polysaccharide comprises the following monosaccharides in mole percentages: 0.11% ribose, 0.11% rhamnose, 0.45% arabinose, 0.13% xylose, 14.50% mannose, 83.96% glucose, and 0.73% galactose. The extraction method does not affect the biological activity of the *Cordyceps militaris* medium polysaccharide P1; the obtained purified polysaccharide P1 has high purity and stable properties, and has significant effects on resistance to oxidation, lowering uric acid and bacteriostasis, which are beneficial to human metabolism; due to the low cost, the purified polysaccharide P1 can be further used in the development of health products, drugs and cosmetics.

10 Claims, 4 Drawing Sheets

CORDYCEPS MILITARIS MEDIUM POLYSACCHARIDE, METHOD FOR SEPARATING AND PURIFYING SAME, AND USE THEREOF

CROSS-REFERENCE TO RELATED APPLICATIONS

This is the U.S. National Stage of International Patent Application No. PCT/CN2018/120506 filed on Dec. 12, 2018, which in turn claims the benefit of Chinese Patent Application No. 201810389081.7 filed on Apr. 27, 2018.

TECHNICAL FIELD

The present invention relates to a *Cordyceps militaris* medium polysaccharide, a method for separating and purifying same, and the use thereof.

BACKGROUND ART

Polysaccharide, also called polyshvacchdrye, is a linear or branched chain polymer linked by aldose or ketose through glycosidic bonds, and polysaccharide is a polar complex macromolecule with a polymerization degree of more than 10 and a molecular weight of generally at least tens of thousands, and is one of the four basic substances involved in life activities. In addition to existing in a free state, the polysaccharide in organisms can also bind to a protein or a lipid to form a proteoglycan and a lipopolysaccharide.

*Cordyceps militaris* (*C. militaris*), also called north *cordyceps*, belongs to Ascomycotina, Pyrenomycetes and Sphaeriales in taxonomy. Both *Cordyceps militaris* and north *cordyceps* belong to Clavicipitaceae, *Cordyceps*, mainly distributed in Northeast, North and Northwest of China. *Cordyceps militaris* can be parasitic on the larvae or pupae of Lepidoptera, Coleoptera, Diptera and other insects, and can be artificially cultivated in batches by using silkworm chrysalis, rice medium and so on.

Due to the limited natural resources of *Cordyceps militaris*, there currently are many artificial cultivation methods, mainly including the following three cultivation methods: (1) collecting wild *Cordyceps militaris* to separate and purify the strains, and then inoculating the *Cordyceps militaris* strains on solid media such as rice and the like containing silkworm chrysalis powder, and cultivating same for 35-45 days under certain temperature, humidity and light conditions to obtain a *Cordyceps militaris* sporocarp; (2) inoculating the *Cordyceps militaris* strains into a larvae or a living pupae of silkworm, and cultivating same for 35-45 days under certain temperature, humidity and light conditions to obtain a *Cordyceps militaris* sporocarp; (3) with soybean powder sucrose or corn syrup sucrose as a medium, cultivating the *Cordyceps militaris* by liquid fermentation.

The production of the *Cordyceps militaris* sporocarp cultivated by artificial methods has been on a considerable scale in China. However, at the same time of harvesting the sporocarp, a large number of *Cordyceps militaris* medium leftovers are also produced, which not only causes environmental pollution, but also is a non-negligible waste of resources.

Studies have shown that cordycepin, *cordyceps* polysaccharide and other bioactive substances are contained in the *Cordyceps militaris* medium leftovers. Thus, in order to better develop and utilize *Cordyceps militaris* resources, improve economic benefits, and improve the industrial chain of *Cordyceps militaris*, it has become necessary to utilize, study and exploit the *Cordyceps militaris* medium leftovers.

Chinese Patent Application (application no. 201110086808.2) discloses a method for extracting a polysaccharide from a *Cordyceps militaris* medium, comprising the steps of using different enzyme solutions to remove proteins and starches in the *Cordyceps militaris* medium, and subjecting same to alcohol precipitation to obtain a *Cordyceps militaris* medium crude polysaccharide. Because the operation is complex, the cost is relatively high and the polysaccharide cannot be further separated and purified, high-purity polysaccharide components cannot be obtained.

SUMMARY OF THE INVENTION

The primary object of the present invention is to provide a *Cordyceps militaris* medium polysaccharide.

Another object of the present invention is to provide a method for separating and purifying the above-mentioned *Cordyceps militaris* medium polysaccharide, comprising the steps of extracting a polysaccharide from a *Cordyceps militaris* waste medium by an ultrasonic-assisted water-extraction and alcohol-precipitation method, and separating and purifying the polysaccharide by an ion exchange chromatography, thereby extracting and separating the polysaccharide components with a relatively high purity and biological activity.

A further object of the present invention is to provide the use of the above-mentioned *Cordyceps militaris* medium polysaccharide.

The objects of the present invention are achieved by the following technical solutions:

a *Cordyceps militaris* medium polysaccharide comprises the following monosaccharides in mole percentages: 0.11% ribose, 0.11% rhamnose, 0.45% arabinose, 0.13% xylose, 14.50% mannose, 83.96% glucose, and 0.73% galactose; the composition of monosaccharides is calculated by a GC-MS area normalization method, which comprises calculating the percentage of the main peak area in the total area by treating all peak areas as 100% except for the solvent peak. It is usually found that the sum of the mole percentages of the monosaccharides is less than 100%, since the unknown samples tested may contain a small amount of monosaccharides other than the standard ones, or there are errors caused by the calculation;

the *Cordyceps militaris* medium polysaccharide has an average molecular weight of 2.18 k Da;

the *Cordyceps militaris* medium polysaccharide comprises a very small amount of sulfate groups, and also comprises pyranose rings and alpha-glucosidic bonds.

A method for separating and purifying the above-mentioned *Cordyceps militaris* medium polysaccharide comprises the following steps:

(1) extraction of the *Cordyceps militaris* medium polysaccharide: drying the *Cordyceps militaris* rice medium leftovers, pulverizing and sieving same to obtain a dry powder of the leftovers; weighing the dry powder and adding 15-16 times distilled water by mass into same, performing an ultrasonic treatment for at least 30 min, performing a reflux extraction at 70° C. for 1.5 h-2.0 h, pooling the extract solutions after several extractions, and filtering the pooled extract and concentrating same to obtain a polysaccharide concentrate; adding 3-4 times of 95% (V/V) ethanol by volume into the polysaccharide concentrate, stirring same, and allowing same to stand overnight at 4° C.; after centrifugation, drying the precipitate to obtain a *Cordyceps militaris* medium polysaccharide extract;

the sieving of step (1) is preferably performed with a 40 mesh screen;

the concentration of step (1) is preferably performed at 50° C.-55° C.;

the centrifugation of step (1) is preferably performed at 5000 r/min for 15 min;

(2) decoloration of the *Cordyceps militaris* medium polysaccharide: dissolving the *Cordyceps militaris* medium polysaccharide extract by adding distilled water, adjusting the pH value to 8.0-8.5, adding $H_2O_2$ solution dropwisely until colorless, and maintaining the temperature at 50° C.-55° C. for at least 2 h;

the concentration of $H_2O_2$ solution of step (2) is preferably 30% (V/V);

(3) deproteinization by the enzymatic method combined with Sevage method:

3-1: mixing a papain solution with the *Cordyceps militaris* medium polysaccharide extract solution, wherein the volume ratio of the two is 1.0:1.5-1.0:1.7, and performing an enzymolysis at 60° C.-70° C. for 2 h-3 h;

the papain solution is prepared in PBS buffer with a pH value of 6.0, wherein the concentration of the papain is 250 U/ml;

3-2: mixing a Sevage reagent with the solution obtained by the enzymolysis at a volume ratio of 1:5, culturing same with shaking for at least 30 min, then centrifuging for multiple times until no protein is precipitated out; and drying the supernatant to obtain a crude *Cordyceps militaris* medium polysaccharide;

the Sevage reagent of step (3) is prepared from chloroform and n-butanol at a volume ratio of 5:1;

in the culturing with shaking step of step (3), the rotating speed of the shaking bed is preferably 150 r/min;

the centrifugation in step (3) is preferably performed at 4000 r/min for 20-30 min;

(4) separation and purification of the *Cordyceps militaris* medium polysaccharide: dissolving the crude *Cordyceps militaris* medium polysaccharide with distilled water, then loading same to DEAE agarose gel FF (DEAE Sephrose Fast Flow) ion exchange chromatography column, and eluting same with distilled water to obtain the *Cordyceps militaris* medium polysaccharide P1.

The separation and purification of the polysaccharide not only removes impurities, but also separates the mixed polysaccharides into individual polysaccharides. The column chromatography comprises an ion exchange chromatography and a gel column chromatography. The ion exchange chromatography performs fractionation based on different charge densities of ions to. The charged group of the anion exchanger is positively charged and the counter ion is negatively charged. Therefore, such an exchanger can undergo an exchange reaction with the negatively charged compounds or anions in the solution, while the cation exchanger is on the contrary.

The *Cordyceps militaris* medium polysaccharide of the present invention can be used as an antioxidant or a bacteriostatic agent, and can also be used for preparing a uric acid lowering drug.

The present invention uses water extraction and alcohol precipitation to obtain the *Cordyceps militaris* medium crude polysaccharide and the ion exchange chromatography column to separate and purify the crude polysaccharide, which has the following advantages and effects over the prior art:

(1) the present invention makes full use of the medium leftovers produced in the cultivation of *Cordyceps militaris*, conforming to the green environmental protection concept of turning waste into wealth, establishes a complete and feasible technical route for the extraction, separation and purification, and the study of physical and chemical properties, structure and biological activity of the *Cordyceps militaris* medium polysaccharide, improves the residue treatment process for the industry of artificial cultivation of *Cordyceps militaris*, and provides the technical guidance for the extraction, separation and purification of edible fungus polysaccharide.

(2) The water-extraction and alcohol-precipitation method of the present invention can achieve large-flux polysaccharide extraction, which has the advantages of low cost, good repeatability and high yield, and is suitable for industrial large-scale production.

(3) The DEAE Sephrose Fast Flow used in the present invention has better physical and chemical stability and mechanical properties, possesses large exchange capacity, and can be cleaned in situ; the bed volume changes little with the ion strength of pH; due to the high flow rate and load, it is suitable for the purification of a large number of crude products.

(4) The extraction method of the present invention does not affect the biological activity of the *Cordyceps militaris* medium polysaccharide P1; the obtained purified polysaccharide P1 has high purity and stable properties, and has significant effects on resistance to oxidation, lowering uric acid and bacteriostasis, which are beneficial to human metabolism; due to the low cost, the purified polysaccharide P1 can be further used in the development of health products, drugs and cosmetics.

(5) The present invention creatively combines water extraction and alcohol precipitation extraction with the ion exchange chromatography separation and purification of polysaccharide for the study of polysaccharide produced from the *Cordyceps militaris* medium leftovers, derives good process parameters, and selects DEAE Sephrose Fast Flow as a chromatographic column packing, which provide a technical guidance and new ideas for the extraction, separation and purification of the polysaccharide from the *Cordyceps militaris* medium leftovers.

DETAILED DESCRIPTION OF EMBODIMENTS

The present invention will be further described in detail below in conjunction with examples and accompanying drawings, but this does not limit the implementation of the present invention.

In the present invention, the analysis on the physical and chemical properties of the *Cordyceps militaris* medium polysaccharide is carried out by China National Analytical Center, Guangzhou, with the report number of 2018001306-1 b.

Example 1

Figure 1:
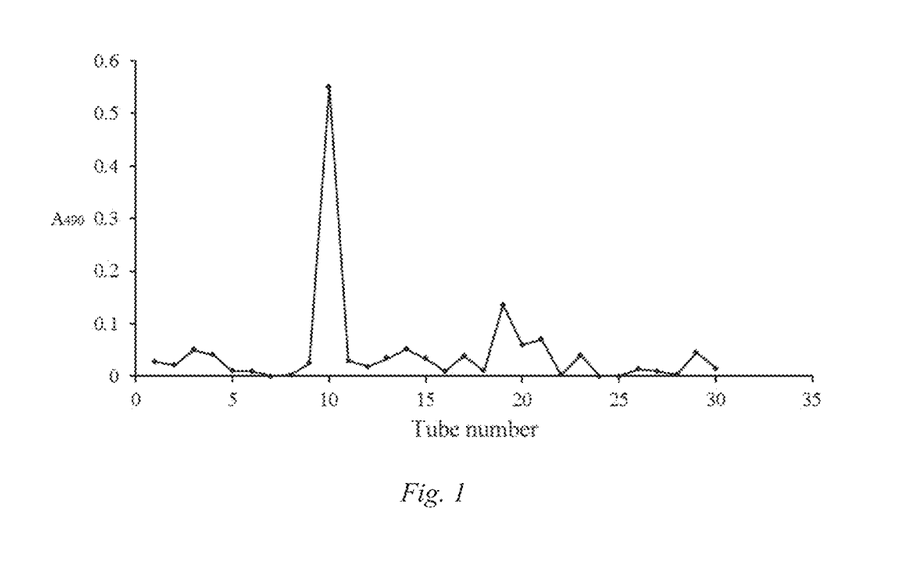
FIG. 1 is an elution curve of the *Cordyceps militaris* medium polysaccharide.

A method for extracting, separating and purifying polysaccharide from *Cordyceps militaris* medium leftovers comprises the following steps:

(1) extraction of *Cordyceps militaris* medium polysaccharide: weighing 55 g of *Cordyceps militaris* rice medium leftovers, fully drying, pulverizing, and sieving same with a 40 mesh screen; weighing 50 g of the dried powder and adding 800 ml of distilled water into same, performing an ultrasonic treatment for 30 min, performing a reflux extraction at 70° C. for 1.5 h, pooling the filtrates after 3 extractions, and concentrating same to 100 ml at 55° C. after vacuum suction filtration to obtain a polysaccharide concentrate; adding 400 ml of 95% ethanol into the polysaccharide concentrate, continuously stirring same to make the polysaccharide precipitate evenly, and allowing same to stand overnight at 4° C.; after centrifugation at 5000 r/min for 15 min, drying the precipitate to obtain a *Cordyceps militaris* medium polysaccharide extract;

(2) decoloration of the *Cordyceps militaris* medium polysaccharide: dissolving the *Cordyceps militaris* medium polysaccharide extract by adding distilled water, and preparing same into a polysaccharide extract solution with a concentration of 0.05 g/ml, adding NaOH to adjust the pH value to 8.0, adding 30% $H_2O_2$ dropwisely until colorless, and maintaining the temperature at 50° C. for 2 h;

(3) deproteinization by the enzymatic method combined with Sevage method:

accurately weighing 0.1 g of papain, dissolving same with PBS buffer with a pH value of 6.0 into a solution with a final concentration of 250 U/ml, mixing same with the *Cordyceps militaris* medium polysaccharide extract solution, wherein the volume ratio of the enzyme solution and the *Cordyceps militaris* medium polysaccharide extract solution is 1.0:1.5, and performing an enzymolysis at 64° C. for 3 h;

mixing a Sevage reagent (chloroform:n-butanol=5:1) with the solution obtained by the enzymolysis with a volume ratio of 1:5, placing same on a shaking bed with a shaking speed at 150 r/min for 30 min, then centrifuging at 4000 r/min for 20 min, and repeating the centrifugation for multiple times until no protein is precipitated out, pooling the supernatant, and drying same at 50° C. to obtain a crude *Cordyceps militaris* medium polysaccharide;

(4) separation and purification of the *Cordyceps militaris* medium polysaccharide:

weighing 0.1 g of the crude *Cordyceps militaris* medium polysaccharide, dissolving same in 10 ml of distilled water, then loading same to DEAE Sephrose Fast Flow ion exchange chromatography column, and eluting same with the distilled water at a flow rate of 0.5 ml/min; collecting one tube of eluent every 10 min, detecting tube by tube the polysaccharide content by a phenol-sulfuric acid method, and pooling the eluents according to the elution curve (FIG. 1) to obtain the *Cordyceps militaris* medium polysaccharide P1.

The specific operations of the phenol-sulfuric acid method to detect the polysaccharide content are as follows: precisely weighing 0.1 g of an anhydrous glucose standard dried at 105° C. to constant weight, placing same into a 100 ml volumetric flask and adding distilled water for dissolution, performing a volumetric dilution, and shaking until uniform to prepare a standard solution (1 mg/ml) for later use; diluting the solution to standard solutions with different concentrations of 10, 20, 40, 60, 80 and 100 µg/ml respectively; pipetting 1 ml each of the above-mentioned solutions and placing same in a test tube, adding 0.5 ml of 6% phenol solution into the tube and mixing same uniformly, then adding 2.5 ml of concentrated sulfuric acid and mixing same uniformly, and allowing same to stand at room temperature for 20 min, measuring the absorbance at 490 nm with the distilled water as the blank control, and drawing a standard curve with the glucose concentration as the horizontal coordinate and the OD value as the vertical coordinate; determining the polysaccharide content in unknown samples by a standard curve method.

The purified *Cordyceps militaris* medium polysaccharide (named as P1) is obtained by freeze-drying the eluted polysaccharide components after concentration and dialysis.

Example 2

The *Cordyceps militaris* medium polysaccharide P1 obtained in example 1 is subjected to an ultraviolet spectrum analysis, wherein the analysis comprises the steps of weighing 1 mg of each of the polysaccharide samples to prepare a polysaccharide solution with a concentration of 1 mg/mL, and scanning to obtain an ultraviolet spectrum within 200-800 nm.

Figure 2:
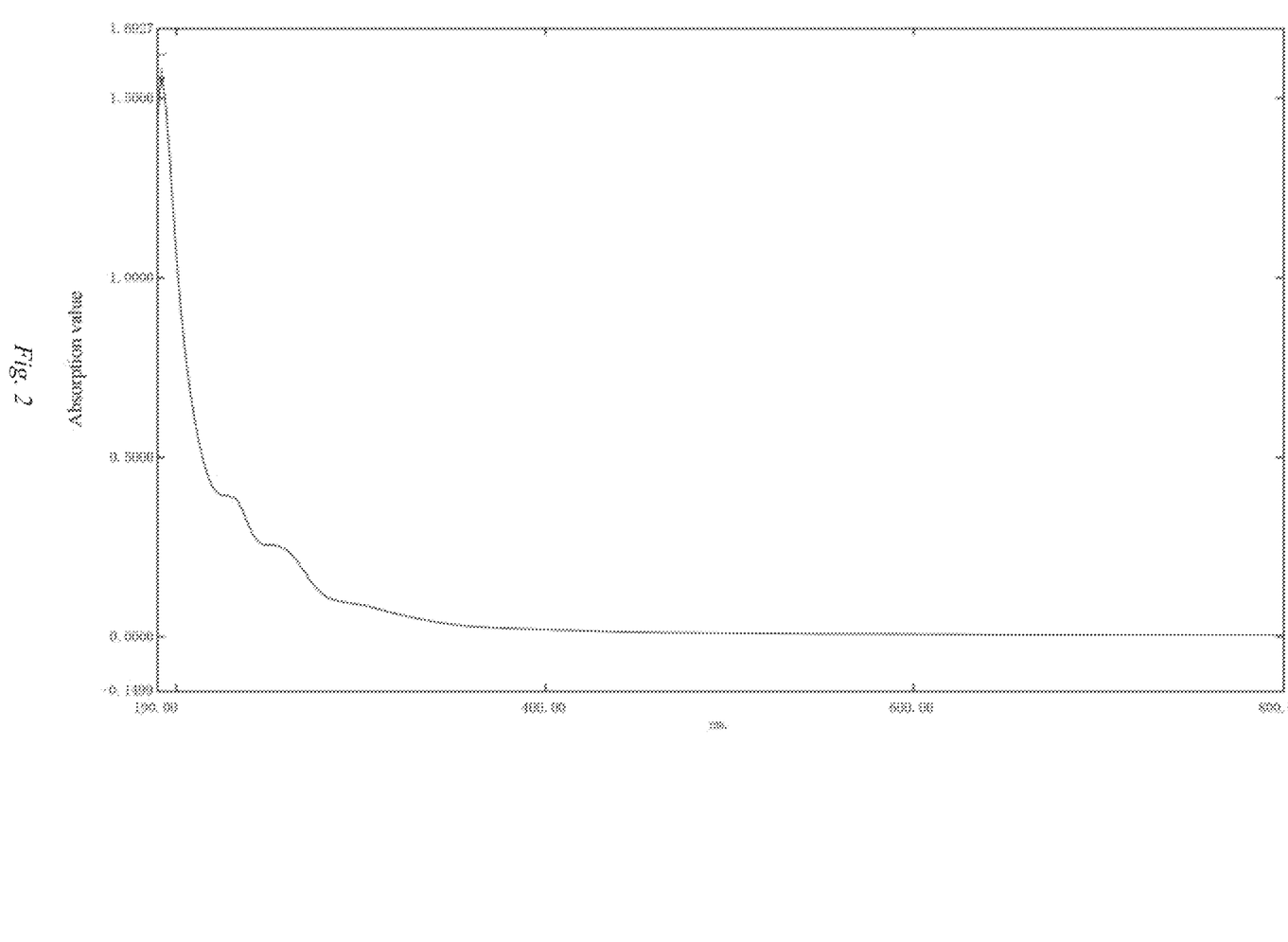
FIG. 2 is an ultraviolet spectrogram of the polysaccharide P1.

FIG. 2 is an ultraviolet spectrogram of P1. The results show that P1 has weak absorption peaks at 260 nm and 280 nm, indicating that P1 contains a small amount of proteins and nucleic acids.

Example 3

The *Cordyceps militaris* medium polysaccharide P1 obtained in example 1 is subjected to an analysis on polysaccharide molecular weight, wherein the specific experimental method is as follows:

using a gel permeation chromatography (GPC) to determine the molecular weight; weighing 2 mg of the freeze-dried polysaccharide sample, adding 0.02 M of a phosphoric acid buffer solution for dissolution, preparing same into a solution with a concentration of 2.0 mg/mL, and performing filtration with 0.22 µm sterile filter membrane to obtain a filtrate for later use;

chromatographic conditions: column temperature 35° C.; 0.02 mol/L of the phosphate buffer (pH 7.0) as a mobile phase, flow rate 0.6 ml/min, loading amount 20 µL; TSK gel protection column (40 mm×6.0 mm), TSKG-4000K gel column (300 mm×7.8 mm) and TSKG-2500K gel column (300 mm×7.8 mm); Waters 2414 differential refraction detector to perform detection; preparing a series of dextran solutions with different molecular weights (700, 400, 200, 100, 50, 30, 10, 5 kD) as standard samples to draw a standard curve. The molecular weight of the sample is calculated according to the corresponding elution volume by comparison to the standard curve.

The results show that the *Cordyceps militaris* medium polysaccharide P1 has an average molecular weight of 2.18 k Da.

Example 4

The *Cordyceps militaris* medium polysaccharide P1 obtained in example 1 is subjected to an analysis on composition of monosaccharides, wherein the specific method is as follows:

weighing 10 mg of the polysaccharide sample, adding 5 mL of trifluoroacetic acid (4 M) into same, and performing hydrolysis at 110° C. for 2 h; performing vacuum rotatory evaporation on the hydrolysate for drying at 50° C., and washing same with the chromatographic pure methanol for 3 times (adding chromatographic pure methanol, and then repeating the rotary drying for 3 times until there is no smell of trifluoroacetic acid from the rotary dried substances) to obtain a polysaccharide hydrolysate;

sequentially adding 10 mg of hydroxylamine hydrochloride, 1 mg of internal standard inositol and 2 mL of pyridine into the polysaccharide hydrolysate, sealing same, performing water bath at 90° C. for 30 min, then adding 2 mL of acetic anhydride and performing water bath at 90° C. for 30 min again, and adding 2 mL of water to stop the reaction; adding 2 mL of dichloromethane for extraction with 2 repeats, combining the dichloromethane phase, adding anhydrous sodium sulfate for dryness, and filtering same through a 0.22 μm organic microporous membrane for later use;

using a gas chromatograph for analysis, with the analytical column being HP-5MS quartz capillary column (30 m×0.25 mm×0.25 μm). The temperature program is as follows: sample inlet temperature 250° C., initial column temperature 100° C., holding for 0.5 min; then rising the temperature to 140° C. at 20° C./min, holding for 5 min; rising the temperature to 160° C. at a speed of 3° C./min; and then rising the temperature to 250° C. at a speed of 10° C./min, holding for 5 min. The sample loading volume is 1 μL; the split ratio is 10:1; the mobile phase is helium; the flow rate is 1 mL/min.

Various kinds of monosaccharide standards (rhamnose, arabinose, ribose, xylose, mannose, glucose and galactose) are tested by the same steps, and the treated standard monosaccharides are analyzed by the gas chromatograph according to the detecting procedure.

The results of the monosaccharide composition of the *Cordyceps militaris* medium polysaccharide measured are shown in the following table:

TABLE 1

The monosaccharide composition of the Cordyceps militaris medium polysaccharide P1

| Component | Mole percentage (%) | | | | | | |
| --- | --- | --- | --- | --- | --- | --- | --- |
| | Ribose | Rhamnose | Arabinose | Xylose | Mannose | Glucose | Galactose |
| P1 | 0.11 | 0.11 | 0.45 | 0.13 | 14.50 | 83.96 | 0.73 |

Example 5

The *Cordyceps militaris* medium polysaccharide P1 obtained in example 1 is subjected to a fourier infrared spectroscopy analysis:

weighing 2 mg of the polysaccharide sample, mixing same uniformly with dried KBr (potassium bromide) in a mortar, grinding and tabletting same by a tabletting machine, and using the fourier transform infrared spectrometer to scan in a wave number range of 400-4000 $cm^{-1}$.

Figure 3:
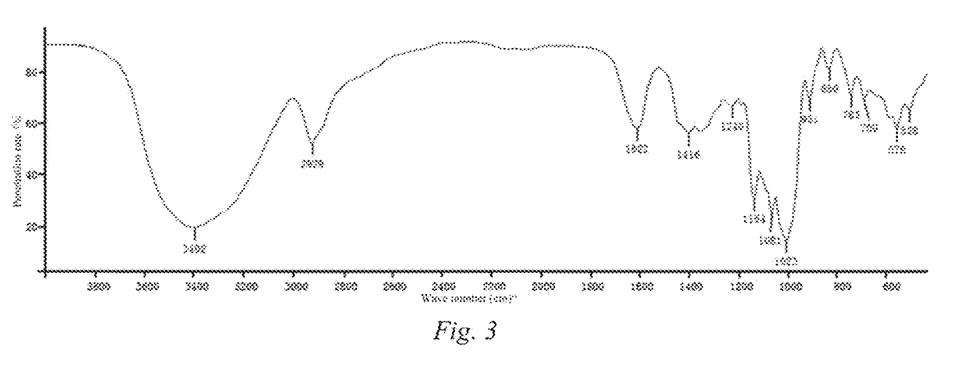
FIG. 3 is an infra-red spectrogram of the polysaccharide P1.

FIG. 3 is an infra-red spectrogram of P1. The peaks at 3402 $cm^{-1}$ and 3401 $cm^{-1}$ are respectively generated by O—H stretching vibration of P1; the peak at 2929 $cm^{-1}$ is generated by C—H vibration; and the peaks at 1622 $cm^{-1}$ and 1642 $cm^{-1}$ are respectively generated by C=O stretching vibration of P1, which are all characteristic peaks of polysaccharides, indicating that P1 belongs to polysaccharides.

In addition, in the infrared spectrum of P1, the weak peak at 1240 $cm^{-1}$ is generated by S=O stretching vibration, suggesting that there is a very small amount of sulfate groups in P1; the peak at 1154 $cm^{-1}$ is the absorption peak of C—O on a ring, and the peaks at 1081 $cm^{-1}$ and 1023 $cm^{-1}$ are generated by the deviational vibration of alcoholic hydroxyl groups, these three peaks suggesting the existence of pyranose rings in P1; and the peak at 850 $cm^{-1}$ indicates the existence of alpha-glucosidic bonds in P1.

Example 6

The *Cordyceps militaris* medium polysaccharide P1 obtained in example 1 is subjected to analysis of antioxidant ability:

(1) Analysis of ABTS Free Radical Scavenging Ability:

mixing 5 mL of each of 7 mmol/L ABTS aqueous solution with 2.45 mmol/L of potassium persulfate aqueous solution, placing the mixture in dark for reaction for 12 h to obtain ABTS free radicals, and diluting the ABTS free radical solution so that its absorbance value becomes 0.70±0.02 at 734 nm wavelength. The absorbance value at 734 nm is measured after uniformly mixing 1 mL of the *Cordyceps militaris* medium polysaccharide P1 solution at different mass concentrations with 2 mL of the ABTS free radical solution for 10 min, which is recorded as $A_1$; the absorbance value at 734 nm is measured after mixing 2 mL of the ABTS free radical solution with 1 mL of distilled water, which is recorded as $A_0$; the absorbance value at 734 nm is measured after mixing 2 mL of distilled water with 1 mL of the polysaccharide solution, which is recorded as $A_2$.

Scavenging rate (%): $Y=[1-(A_1-A_2)/A_0]\times 100\%$

Figure 4:
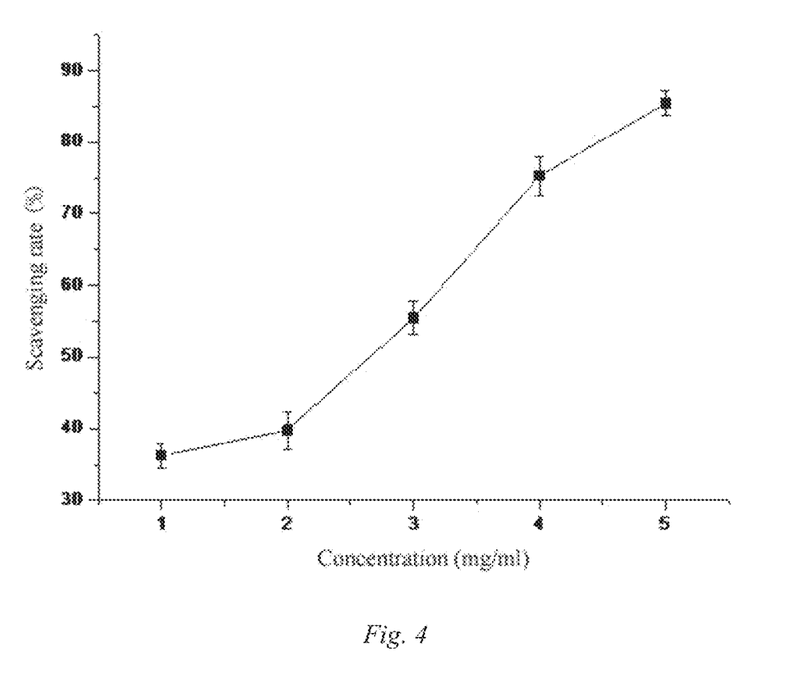
FIG. 4 shows the ABTS free radical scavenging ability of the polysaccharide P1.

FIG. 4 shows the ABTS free radical scavenging ability of the *Cordyceps militaris* medium polysaccharide P1. It can be seen from FIG. 4 that in the concentration range of 1.0-5.0 mg/ml, the *Cordyceps militaris* medium polysaccharide (P1) components have an outstanding ABTS free radical scavenging ability, and have a positive correlation with the polysaccharide concentration. When the polysaccharide concentration is 5.0 mg/ml, the ABTS free radical scavenging rate of P1 is 85.4%.

(2) Analysis of OH Free Radical Scavenging Ability:

adding 1 mL of the *Cordyceps militaris* medium polysaccharide P1 solution at different concentrations, 1 mL of 6 mmol/L $FeSO_4$ solution, 1 mL of 6 mmol/L $H_2O_2$ solution and 1 mL of 6 mmol/L of salicylic acid-ethanol solution into test tubes, respectively, performing water bath at 37° C. for 1 h, and measuring the absorbance $A_i$ at 510 nm. $A_0$ is measured with distilled water instead of the sample solution, and $A_j$ is measured with distilled water instead of the $H_2O_2$ solution.

Scavenging rate (%)=$[1-(A_i-A_j)/A_0]\times 100\%$

Figure 5:
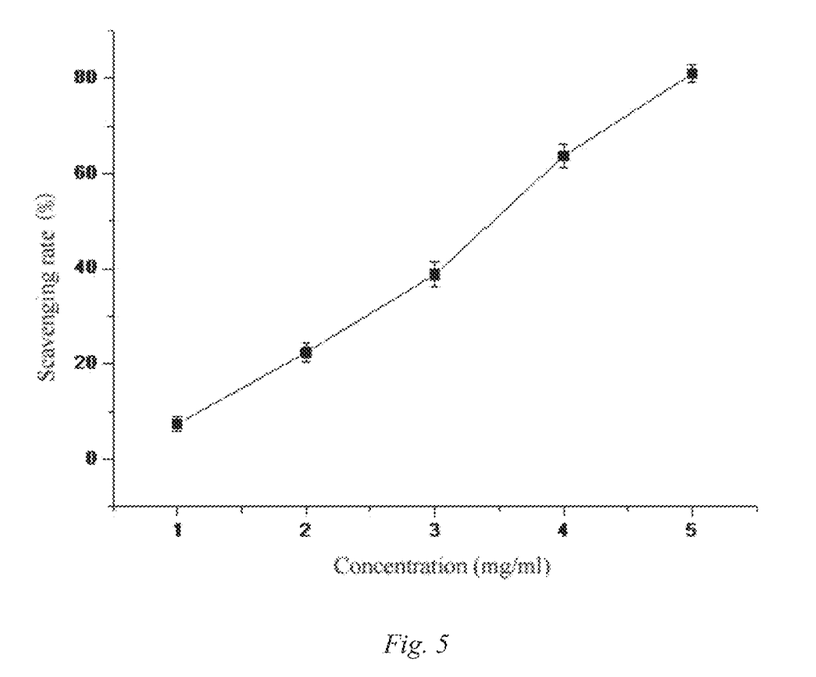
FIG. 5 shows the OH free radical scavenging ability of the polysaccharide P1.

FIG. 5 shows the OH free radical scavenging ability of the *Cordyceps militaris* medium polysaccharide P1. It can be seen from FIG. 5 that the *Cordyceps militaris* medium polysaccharide (P1) components have an outstanding OH free radical scavenging ability; in the mass concentration range of 1.0-5.0 mg/ml, the ability of P1 to scavenge OH free radicals enhances gradually with the increase of the solution concentration; when the concentration is 5.0 mg/ml, the scavenging rate can reach 81.03%.

Example 7

Uric acid lowering ability of the *Cordyceps militaris* medium polysaccharide P1 obtained in example 1 is studied:
(1) Establishment of a Hyperuricemia Model Sixty male mice are randomly divided into six groups after one week's feeding, with 10 mice in each group, including a blank group, a model group, a high P1 dose group (400 mg/kg), a middle P1 dose group (200 mg/kg), a low P1 dose group (100 mg/kg) and a positive drug (50 mg/kg) control group. Every morning, the model group, the positive control group and the high, middle and low P1 dose groups are administered with 600 mg/kg of xanthine (ig) by gavage+100 mg/kg of oteracil potassium (ip) by intraperitoneal injection, fasting but water available for one hour before the model is made, and the blank group is administered with the same dose of normal saline. In the afternoon, the high, middle and low P1 dose groups are administered with the polysaccharide suspension by gavage; the positive control group is administered with 50 mg/kg of allopurinol suspension by gavage; the model group and the blank group are administered with the same volume of normal saline by gavage for seven consecutive days.

(2) Determination of Biochemical Indexes In Vivo

On the seventh day, 1 hour after administration in the afternoon, the mice are weighed and decapitated for blood collection. The blood is centrifuged at 3000 r/min for 10 min after being placed at room temperature for 40 min, and the upper layer of the serum is pipetted. Serum uric acid (UA), serum creatinine (CREA) and serum urea nitrogen (BUN) values are measured by kits to investigate the effects of the polysaccharide P1 on UA, CREA and BUN, as well as renal functions in the hyperuricemia model mice.

The results of the uric acid lowering effect of the *Cordyceps militaris* medium polysaccharide P1 measured are shown in the following table:

It can be seen from table 2 that compared with the normal group, the levels of serum creatinine, serum uric acid and serum urea nitrogen in the model group all increase significantly, indicating the success of the model.

Compared with the model group, the low, middle and high P1 dose groups can reduce the level of mice serum creatinine by 5.03%, 20.19% and 32.76%, respectively, reduce the level of mice serum uric acid by 39.58%, 46.46% and 53.72%, respectively, and reduce the level of mice serum urea nitrogen by 22.77%, 40.05% and 51.59%, respectively. The results show that in this experimental model, the *Cordyceps militaris* medium polysaccharide P1 can reduce the levels of serum creatinine, serum uric acid and serum urea nitrogen in mice with hyperuricemia.

Example 8

The *Cordyceps militaris* medium polysaccharide P1 obtained in example 1 is subjected to a bacteriostatic study:

the bacteriostatic activities of *Cordyceps militaris* medium polysaccharide P1 on the common pathogenic bacteria *Staphylococcus aureus* (Sa) and *Pseudomonas aeruginosa* (Pa) are determined by a drilling method. The main operations are as follows: pouring mediums into culture plates with a diameter of 90 mm, pipetting 150 μl of the bacterial suspension on the plates, and coating the bacterial suspension on same evenly; then drilling four holes in each plate with an 8 mm driller, respectively adding 40 μl of 1 mg/ml standby *Cordyceps militaris* medium polysaccharide P1, and adding 40 μl of normal saline into each hole in the control group. The plates are placed in a constant temperature incubator at 37° C. for 24 h, and a cross method is used to respectively measure the diameters of each bacteriostatic circle on the test plate and the control plate, and the average value is calculated.

Figure 6:
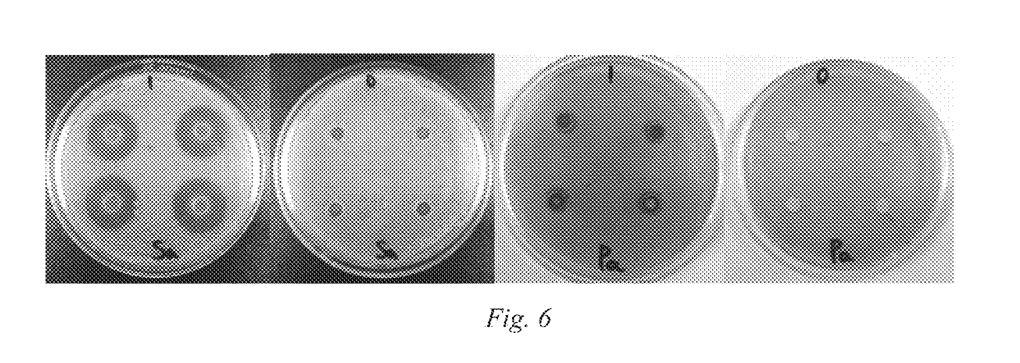
FIG. 6 is a graph showing the bacteriostasis experiment results of the polysaccharide P1, wherein Sa-a bacteriostatic circle against *Staphylococcus aureus*; Pa-a bacteriostatic circle against *Pseudomonas aeruginosa;* 1-a bacteriostatic circle produced by the polysaccharide P1; 0-a bacteriostatic circle of the control group.

The bacteriostatic results of the polysaccharide P1 are shown in FIG. 6, which are respectively the bacteriostatic results of P1 against *Staphylococcus aureus*, *Staphylococcus aureus* control group, *Pseudomonas aeruginosa*, and *Pseudomonas aeruginosa* control group. The diameters of the bacteriostatic circles measured are shown in Table 3.

TABLE 3

| | Diameter of bacteriostatic circle (cm) | |
|---|---|---|
| | *Staphylococcus aureus* | *Pseudomonas aeruginosa* |
| P1 | 2.14 ± 0.08 | 1.25 ± 0.14 |

TABLE 2

The uric acid lowering effect of the *Cordyceps militaris* medium polysaccharide P1

| Group | Dosage | CREA (μmol/L) | UA (μmol/L) | BUN (mmol/L) |
|---|---|---|---|---|
| Normal group | / | 52.23 ± 7.73** | 76.72 ± 7.29** | 6.12 ± 0.68** |
| Model group | 100a + 600b | 90.65 ± 14.20 | 194.56 ± 20.10 | 12.91 ± 1.40 |
| Positive group | 50 | 71.69 ± 8.43** | 108.83 ± 6.53** | 6.99 ± 1.10** |
| High dose group | 400 | 66.73 ± 9.35** | 90.96 ± 9.89** | 6.25 ± 0.94** |
| Middle dose group | 200 | 72.34 ± 9.12** | 105.24 ± 7.55** | 7.74 ± 0.84** |
| Low dose group | 100 | 86.09 ± 10.19 | 118.77 ± 7.03** | 9.97 ± 1.00** |

It can be seen from table 3 that the *Cordyceps militaris* medium polysaccharide P1 can inhibit *Staphylococcus aureus* and *Pseudomonas aeruginosa* in different levels, wherein the inhibition on *Staphylococcus aureus* is stronger than that on *Pseudomonas aeruginosa*.

The above examples are preferred implementations of the present invention. However, the implementation of the present invention is not limited by the above examples, and any alternation, modification, substitution, combination and simplification without departing from the spiritual essence and principles of the present invention should all be equivalent replacements, and all fall within the scope of protection of the present invention.

The invention claimed is:

1. A method for separation and purification of a *Cordyceps militaris* medium polysaccharide, comprising the following steps:
   (1) extraction of the *Cordyceps militaris* medium polysaccharide: drying the *Cordyceps militaris* rice medium leftovers, pulverizing and sieving same to obtain a dry powder of the leftovers; weighing the dry powder and adding 15-16 times distilled water by mass into same, performing an ultrasonic treatment for at least 30 min, performing a reflux extraction at 70° C. for 1.5 h-2.0 h, pooling the extract solutions after several extractions, and filtering the pooled extract and concentrating same to obtain a polysaccharide concentrate; adding 3-4 times of 95% (V/V) ethanol by volume into the polysaccharide concentrate, stirring same, and allowing same to stand overnight at 4° C.; after centrifugation, drying the precipitate to obtain a *Cordyceps militaris* medium polysaccharide extract;
   (2) decoloration of the *Cordyceps militaris* medium polysaccharide: dissolving the *Cordyceps militaris* medium polysaccharide extract by adding distilled water, adjusting the pH value to 8.0-8.5, adding $H_2O_2$ solution dropwisely until colorless, and maintaining the temperature at 50° C.-55° C. for at least 2 h;
   (3) deproteinization by an enzymatic method combined with Sevage method:
   3-1: mixing a papain solution with the *Cordyceps militaris* medium polysaccharide extract solution, wherein the volume ratio of the two is 1.0:1.5-1.0:1.7, and performing an enzymolysis at 60° C.-70° C. for 2 h-3 h;
   3-2: mixing a Sevage reagent with the solution obtained by the enzymolysis at a volume ratio of 1:5, culturing same with shaking for at least 30 min, then centrifuging for multiple times until no protein is precipitated out; and drying the supernatant to obtain a crude *Cordyceps militaris* medium polysaccharide;
   (4) separation and purification of the *Cordyceps militaris* medium polysaccharide: dissolving the crude *Cordyceps militaris* medium polysaccharide with distilled water, then loading same to DEAE agarose gel FF ion exchange chromatography column, and eluting same with distilled water to obtain the polysaccharide.

2. The method for separation and purification according to claim 1, characterized in that the concentration of step (1) is performed at 50° C.-55° C.

3. The method for separation and purification according to claim 1, characterized in that the concentration of $H_2O_2$ solution in step (2) is 30% (V/V).

4. The method for separation and purification according to claim 1, characterized in that the papain solution of step (3) is prepared in PBS buffer with a pH value of 6.0, wherein the concentration of the papain is 250 U/ml.

5. The method for separation and purification according to claim 1, characterized in that the Sevage reagent of step (3) is prepared from chloroform and n-butanol at a volume ratio of 5:1.

6. A method for scavenging free radicals, comprising:
   adding *Cordyceps militaris* medium polysaccharide prepared by the method according to claim 1 into a ABTS or OH free radical containing solution.

7. A method for lowering uric acid in a subject, comprising:
   administering *Cordyceps militaris* medium polysaccharide prepared by the method according to claim 1 to the subject.

8. The method for separation and purification according to claim 1, wherein the *Cordyceps militaris* medium polysaccharide comprises the following monosaccharides in mole percentages: 0.11% ribose, 0.11% rhamnose, 0.45% arabinose, 0.13% xylose, 14.50% mannose, 83.96% glucose, and 0.73% galactose.

9. The method for separation and purification according to claim 1, wherein the *Cordyceps militaris* medium polysaccharide has an average molecular weight of 2.18 k Da.

10. The method for separation and purification according to claim 1, wherein the *Cordyceps militaris* medium polysaccharide comprises sulfate groups, pyranose rings and alpha-glucosidic bonds.

* * * * *